(12) United States Patent
Ein-Gal

(10) Patent No.: US 8,488,741 B2
(45) Date of Patent: Jul. 16, 2013

(54) ADEQUATE CLEARANCE FOR GANTRY TRAJECTORY

(76) Inventor: Moshe Ein-Gal, Ramat Hasharon (IL)

( * ) Notice: Subject to any disclaimer, the term of this patent is extended or adjusted under 35 U.S.C. 154(b) by 289 days.

(21) Appl. No.: 12/972,673

(22) Filed: Dec. 20, 2010

(65) Prior Publication Data

US 2012/0155611 A1    Jun. 21, 2012

(51) Int. Cl.
*H05G 1/54*    (2006.01)

(52) U.S. Cl.
USPC ................................................ 378/117

(58) Field of Classification Search
USPC ................... 378/20, 68, 117, 208, 65
See application file for complete search history.

(56) References Cited

U.S. PATENT DOCUMENTS

2011/0006230 A1*    1/2011  Fadler ...................... 250/522.1

* cited by examiner

*Primary Examiner* — Courtney Thomas
(74) *Attorney, Agent, or Firm* — Dekel Patent Ltd.; David Klein

(57) ABSTRACT

A method including irradiating a target, which is located in a patient supported by a movable table, with a radiation beam emanating from a radiation source located in a movable gantry, and positioning the gantry and the table so as to maintain adequate clearance, wherein a clearance is defined as a distance between the gantry and the patient or the table, whichever is smaller, and wherein adequate clearance is defined as a clearance that alleviates a risk of a collision between the gantry and the patient or the table during movement of the gantry.

13 Claims, 2 Drawing Sheets

ADEQUATE CLEARANCE FOR GANTRY TRAJECTORY

FIELD OF THE INVENTION

The present invention generally relates to a system and method for radiation therapy or diagnostics, and particularly to modifying a position of a target relative to the trajectory of a radiation beam gantry so as to increase clearance between the gantry and the patient or couch.

BACKGROUND OF THE INVENTION

An isocentric system typically includes a radiation head mounted on a rotatable gantry. A radiation source is disposed in the radiation head and produces a radiation beam. The gantry rotates about a rotational axis such that the radiation beam intersects the rotational axis at an isocenter. A patient, supported on a couch or table (the terms being used interchangeably), is placed such that a target to be irradiated in the patient is at the isocenter, which enables irradiating the target from various angles. A typical distance between the radiation source and the isocenter of an isocentric linear accelerator (LINAC) system is 1 m.

Clearance is the distance between the radiation head and the patient or the couch, whichever is smaller. Such patient-dependent clearance may vary with gantry rotation and/or with couch positioning. Insufficient clearance for a range of gantry angles amounts to a collision between the radiation head and the patient or couch. The angular positions of the gantry where collision would occur are thus excluded from the arc treatment plan. Attaching external devices such as collimators or wedges to the radiation head further reduces the clearance and may exclude a wider range of gantry angles from being used in the arc treatment plan.

SUMMARY OF THE INVENTION

The present invention seeks to provide an improved system and method for radiation therapy or diagnostics, wherein the position of the target is modified relative to the trajectory of a radiation beam gantry so as to provide adequate clearance between the radiation head and the patient or the couch, as is described more in detail hereinbelow. The invention reduces the angular positions of the gantry where collision would occur, and thus increases the range of angular positions of the gantry for an arc treatment plan. This may significantly increase the possibilities of beam angles towards the target and reduce radiation to healthy tissue.

The invention provides a method and system for providing adequate clearance of radiation systems. This allows mounting external device on the radiation head without compromising the ability to deliver arc treatment. The method is described with reference to an isocentric system incorporating a gantry rotating about a horizontal rotational axis, but the method applies to any treatment system with relative motion between a radiation head and a target. The method includes simultaneous positioning of the radiation source and the patient such that the distance from the radiation source to the target is greater than that to the isocenter, while the requirement of the beam being directed at the isocenter is relaxed. Beam direction is allowed to be not exactly toward the isocenter but close to it. This relaxation allows simpler motion (trajectory and velocity profile) of the gantry and/or the table. Small deviations of target direction relative to isocenter direction are compensated by the collimator directing the beam toward the actual target location.

There is thus provided in accordance with a non-limiting embodiment of the present invention a method including irradiating a target, which is located in a patient supported by a movable table, with a radiation beam emanating from a radiation source located in a movable gantry, and positioning the gantry and the table so as to maintain adequate clearance, wherein a clearance is defined as a distance between the gantry and the patient or the table, whichever is smaller, and wherein adequate clearance is defined as a clearance that alleviates the risk of a collision between the gantry and the patient or the table during movement of the gantry.

In accordance with an embodiment of the present invention the gantry rotates about a rotation axis, and adequate clearance is maintained by moving the table during rotation of the gantry.

In accordance with an embodiment of the present invention the radiation beam intersects the rotational axis at an isocenter, and the adequate clearance is obtained by moving the patient away from the isocenter in the general direction of the (e.g., moving) beam.

In accordance with an embodiment of the present invention the target is moved simultaneously with the gantry in a trajectory that maintains the adequate clearance for all gantry orientations, and a collimator is used to direct the radiation beam toward the target.

In accordance with an embodiment of the present invention the patient is moved in a plane perpendicular to the rotational axis during rotation of the gantry.

In accordance with an embodiment of the present invention, the patient is moved along a horizontal or vertical direction during rotation of the gantry.

In accordance with an embodiment of the present invention, the method includes, prior to treatment, defining a gantry trajectory including a sequence of gantry locations respectively corresponding to source locations of the radiation source, and deriving a target trajectory including a sequence of target locations respectively corresponding to the source locations such that the isocenter is generally between each source location and the corresponding target location, and during treatment, moving the radiation source and the target according to their respective trajectories such that the target is generally at one of the target locations at the same time that the radiation source is at the corresponding source location, processing target position relative to the radiation source, and directing the radiation beam by the collimator towards the target.

There is also provided in accordance with a non-limiting embodiment of the present invention a system including a radiation source operable to emit a radiation beam towards a target in a patient, a gantry operable to move the radiation source, a table operable to support and move the patient, wherein a clearance is defined as a distance between the gantry and the patient or the table, whichever is smaller, and a controller in communication with the gantry and the table, wherein the controller is operable to maintain adequate clearance during movement of the gantry. A collimator may be provided to collimate the radiation beam, wherein the controller is also in communication with the collimator.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
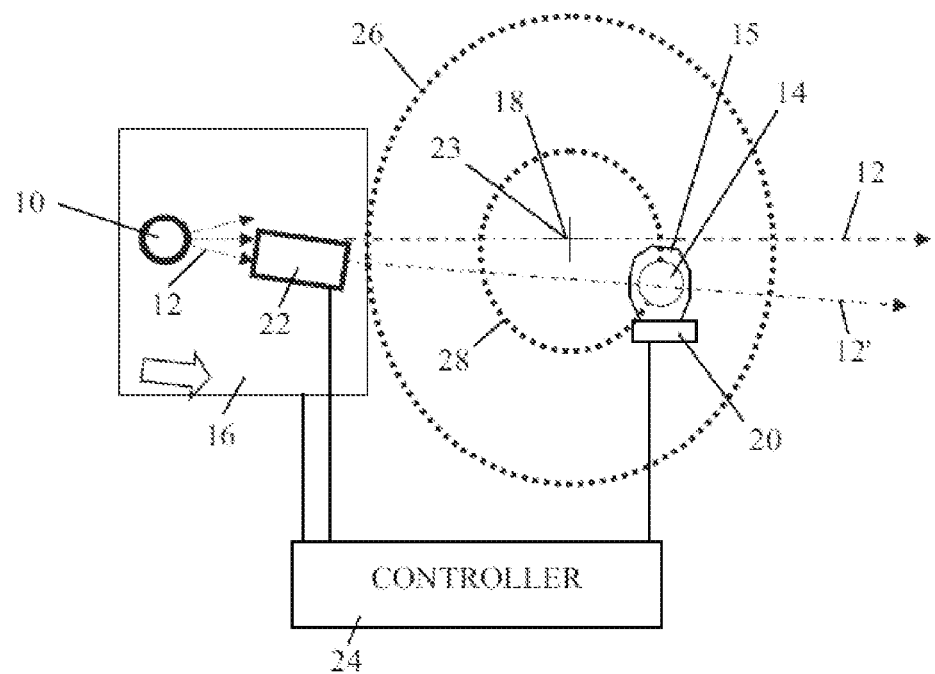
FIG. 1 is a simplified illustration of a system for providing adequate clearance between a gantry and patient or couch, in accordance with an embodiment of the present invention.

Reference is now made to FIG. 1, which illustrates a system for providing adequate clearance between a gantry and patient or couch, in accordance with an embodiment of the present invention.

The system may include a radiation source 10 operable to emit a radiation beam 12 towards a target 14 in a patient 15. A gantry 16 is operable to move radiation source 10. The term "gantry" encompasses any movable structure, such as but not limited to, a movable radiation head, LINAC gantry, CT head and the like. In accordance with the illustrated embodiment, gantry 16 rotates about a rotation axis 18. A table 20 supports and moves the patient 15 (and with it target 14). Table 20 may move in any direction, linear and/or rotational. A collimator 22 may be provided for collimating beam 12.

A clearance is defined as a distance between gantry 16 and patient 15 or table 20, whichever is smaller. "Adequate clearance" is defined as a clearance that alleviates the risk of a collision between gantry 16 and patient 15 or table 20 during movement of gantry 16. Radiation beam 12 intersects rotational axis 18 at an isocenter 23.

A controller 24 is in communication with gantry 16, collimator 22 and table 20. Controller 24 is operable to provide adequate clearance during movement of gantry 16, as is explained below with further reference to FIG. 2.

FIG. 1 illustrates one example of a gantry trajectory 26, namely, a circular gantry trajectory and concentrically circular target trajectory 28. The clearance is increased by moving the patient 15 away from the isocenter 23. In this example, the clearance increase equals the radius of the target trajectory 28. While gantry 16 moves (e.g., rotates), the controller 24 moves target 14 in the same direction and the same angular velocity profile such that a constant clearance increase (which is the adequate clearance) is maintained for all gantry orientations. Table 20 can translate patient 15, as controlled by controller 24, in a plane perpendicular to the rotational axis 18 such that the patient orientation relative to radiation source 10 is similar to that of a stationary patient with the target 14 at the isocenter 23.

Figure 2:
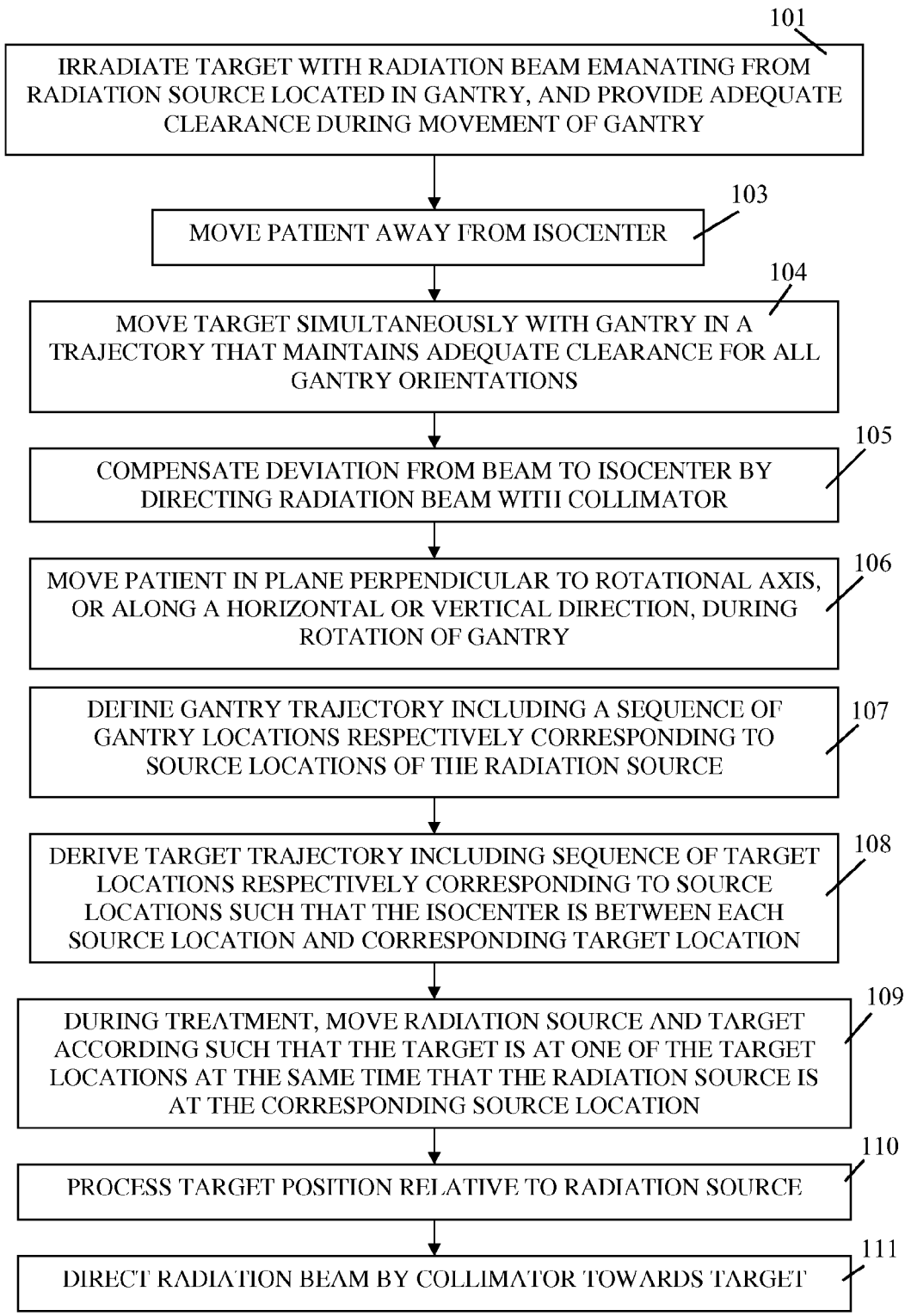
FIG. 2 is a simplified flow chart of a method for providing adequate clearance between the gantry and patient or couch, in accordance with an embodiment of the present invention.

Reference is now made to FIG. 2. In accordance with a non-limiting embodiment of the present invention, the method includes irradiating the target with the radiation beam emanating from the radiation source located in the movable gantry, and providing adequate clearance during movement (e.g., rotation) of the gantry (101).

As described with reference to FIG. 1, the radiation beam intersects the rotational axis at the isocenter. Providing adequate clearance may include moving the patient away from the isocenter (103).

In accordance with an embodiment of the present invention the target is moved simultaneously with the gantry in a trajectory that maintains the adequate clearance for all gantry orientations (104). The deviation from the radiation beam to the isocenter is compensated by directing the radiation beam with the collimator (105). As mentioned before, the patient may be moved in a plane perpendicular to the rotational axis, or along a horizontal or vertical direction, during rotation of the gantry (106).

In accordance with an embodiment of the present invention, prior to treatment, a gantry trajectory is defined including a sequence of gantry locations respectively corresponding to source locations of the radiation source (107). A target trajectory is derived including a sequence of target locations respectively corresponding to the source locations such that the isocenter is generally between each source location and the corresponding target location (108). During treatment, the radiation source and the target are moved according to their respective trajectories such that the target is generally at one of the target locations at the same time that the radiation source is at the corresponding source location (109). The target position relative to the radiation source is processed (110). The radiation beam is then directed by the collimator towards the target (111).

The scope of the present invention includes both combinations and subcombinations of the features described hereinabove as well as modifications and variations thereof which would occur to a person of skill in the art upon reading the foregoing description and which are not in the prior art.

What is claimed is:

1. A method comprising:
   in a system comprising a radiation source operable to emit a radiation beam towards a target in a patient, gantry operable to move the radiation source and a table operable to support and move the patient during irradiation, modifying a position of the target relative to a trajectory of said gantry by positioning said gantry and said table so as to maintain adequate clearance, wherein a clearance is defined as a distance between said gantry and said patient or said table, whichever is smaller, and wherein adequate clearance is defined as a clearance that alleviates a risk of a collision between said gantry and said patient or said table during movement of said gantry.

2. The method according to claim 1, wherein said gantry rotates about a rotation axis, and said adequate clearance is maintained by moving said table during rotation of said gantry.

3. The method according to claim 2, wherein said radiation beam intersects said rotational axis at an isocenter, and wherein said adequate clearance is obtained by moving said target away from said isocenter.

4. The method according to claim 1, further comprising moving said target simultaneously with said gantry in a trajectory that maintains said adequate clearance for all gantry orientations.

5. The method according to claim 2, further comprising compensating for a deviation from the radiation beam to the isocenter by directing said radiation beam with a collimator.

6. The method according to claim 2, further comprising moving the patient generally in a plane perpendicular to said rotational axis during rotation of said gantry.

7. The method according to claim 2, further comprising moving the target substantially along a horizontal or vertical direction during rotation of said gantry.

8. The method according to claim 5, further comprising, prior to treatment:
   defining a gantry trajectory comprising a sequence of gantry locations respectively corresponding to source locations of said radiation source; and
   deriving a target trajectory comprising a sequence of target locations respectively corresponding to the source locations such that the isocenter is generally between each source location and the corresponding target location;
   and during treatment:
   moving said radiation source and said target according to their respective trajectories such that said target is generally at one of the target locations at the same time that said radiation source is at the corresponding source location;

processing target position relative to said radiation source; and directing said radiation beam by said collimator towards said target.

9. A system comprising:
 a radiation source operable to emit a radiation beam towards a target in a patient;
 a gantry operable to move the radiation source;
 a table operable to support and move the patient during irradiation, wherein a clearance is defined as a distance between said gantry and the patient or the table, whichever is smaller, and wherein adequate clearance is defined as a clearance that alleviates a risk of a collision between said gantry and said patient or said table during movement of said gantry; and
 a controller in communication with said gantry and said table, wherein said controller is operable to modify a position of the target relative to a trajectory of said gantry so as to provide said adequate clearance during movement of said gantry.

10. The system according to claim 9, further comprising a collimator operable to collimate said radiation beam, wherein said controller is also in communication with said collimator.

11. The system according to claim 10, wherein said gantry rotates about a rotation axis.

12. The system according to claim 11, wherein the table is operable to move the target in a plane perpendicular to said rotational axis.

13. The system according to claim 9, wherein the controller is also in communication with the radiation source.

* * * * *